United States Patent [19]

Chou

[11] Patent Number: 4,644,060

[45] Date of Patent: Feb. 17, 1987

[54] SUPERCRITICAL AMMONIA TREATMENT OF LIGNOCELLULOSIC MATERIALS

[75] Inventor: Yu-Chia T. Chou, Wilmington, Del.

[73] Assignee: E. I. Du Pont de Nemours and Company, Wilmington, Del.

[21] Appl. No.: 736,386

[22] Filed: May 21, 1985

[51] Int. Cl.$^4$ ............................ A23K 1/22; C08B 1/00
[52] U.S. Cl. ........................................ 536/30; 536/56; 162/72; 162/91; 162/96; 426/69; 426/807
[58] Field of Search .................... 426/69, 807; 536/56; 162/72, 91, 96; 536/30

[56] References Cited

U.S. PATENT DOCUMENTS

| Re. 22,477 | 5/1944 | Millar | 426/69 |
|---|---|---|---|
| 3,259,501 | 7/1966 | Ulrey | 426/69 |
| 4,064,276 | 12/1977 | Conradsen et al. | 426/69 |
| 4,356,196 | 10/1982 | Hultquist | 426/69 |
| 4,385,500 | 5/1983 | Kjelgaard et al. | 426/69 |
| 4,515,816 | 5/1985 | Anthony | 426/69 |

FOREIGN PATENT DOCUMENTS

| 77287 | 4/1983 | European Pat. Off. |
| 2518573 | 6/1983 | France |

OTHER PUBLICATIONS

Ishihara, *Mokuzai Gakkaishi*, 25:804 (1979).
Waagepetersen et al., *Anim. Feed. Sci. Technol.*, 2:131.
Al-Rabbat et al., *Can. J. Anim. Sci.*, 58:443 (1978).
Horton et al., *J. Anim. Sci.*, 48:1239 (1979).
Laksesvela et al., *Anim. Prod.*, 30:437 (1980).
Horton et al., *Can. J. Anim. Sci.*, 61:1059 (1981).
Saenger et al., *J. Anim. Sci.*, 54:419 (1982).

*Primary Examiner*—Ronald W. Griffin

[57] ABSTRACT

The bioavailability of polysaccharide components of lignocellulosic materials can be increased substantially by treatment with ammonia in a supercritical or near-supercritical fluid state.

20 Claims, No Drawings

SUPERCRITICAL AMMONIA TREATMENT OF LIGNOCELLULOSIC MATERIALS

BACKGROUND OF THE INVENTION

The present invention relates generally to biomass conversion methods, and particularly to processes for treating lignocellulosic materials to increase their utility as carbohydrate sources.

Lignocellulosic materials in the form of wood and agricultural wastes represent an unexploited carbohydrate source for microbial fermentation, largely due to the resistance of lignocellulosic substrates to biodegradation. The various polymeric constituents of wood and other fibrous plant materials are intimately associated in a three-dimensional network whose susceptible bonds are largely inaccessible to physical, chemical, or enzymatic attack. In order to render these substances useful as substrates for microbial fermentation, one or more pretreatment processes must be employed to enhance the accessibility of the appropriate chemical bonds. Most known pretreatment strategies rely upon severe conditions, e.g., strong acid or alkali, to degrade lignocellulosic materials. Severe pretreatment processes typically involve large energy expenditures, reactant recycling or disposal problems, or significant capital investment. On the other hand, mild pretreatment systems provide only incremental improvements in the enzymatic or microbial digestibility of lignocellulosic materials. The following patents and publications disclose methods of treating cellulose-containing materials with ammonia or other amines:

Ulrey, U.S. Pat. No. 3,259,501, discloses a method of treating rice hulls involving contact with ammonia or other gaseous nitrogen compounds in a closed reactor, at temperatures from about 50° C. to about 230° C., and at pressures from about 70 kPa (10 psi) to about 6.21 MPa (900 psi). A treatment time of about 30 minutes is disclosed. The resulting treated rice hulls are claimed to be useful as livestock fodder or as a soil conditioner, mulch, or fertilizer.

Hultquist, U.S. Pat. No. 4,356,196, describes a process for treating alfalfa and other cellulosic agricultural crops. In this method, the materials to be treated are contacted with ammonia at pressures from about 203 kPa (30 psi) to about 4.05 MPa (588 psi), and at temperatures from about 10° C. to about 85° C., in a closed reactor, for about 30 minutes. Ammonia is then released from the reactor explosively, leaving a product having enhanced value as a foodstuff for livestock.

Dale, published European Patent Application No. 77,287, discloses a method for increasing the reactivity of cellulose, for example, cellulose-containing feeds such as alfalfa hay, involving contact with a cellulose-swelling agent, for example, gaseous or liquid ammonia, at a pressure from about 1.137 MPa (165 psi) to about 1.241 MPa (180 psi), and at a temperature of about 25° C., for about 30 minutes. Pressure is then explosively released, providing a material with an expanded fiber structure.

Gallo, French Patent No. 2,518,573, discloses a process for saccharification of lignocellulosic materials involving pretreatment with an amine, for example, diethanolamine, for about 1 to 3 hours at a temperature from about 80° C. to about 170° C., followed by enzymatic hydrolysis.

A greatly improved process for pretreating wood and other lignocellulosic materials has now been developed, which relies upon use of ammonia in a supercritical or near-supercritical state to render the polymeric components of lignocellulosic materials susceptible to enzymatic hydrolysis. Ammonia exists as a supercritical fluid when maintained at a temperature greater than 132.4° C., at a pressure greater than 11.28 MPa (1636 psi), and at a density greater than 0.235 g/mL. Lignocellulosic materials treated by the process of the present invention can be nearly completely hydrolyzed by cellulases, employed directly as carbohydrate sources for microbial fermentation, or fed to livestock.

SUMMARY OF THE INVENTION

The present invention provides a process for improving the bioavailability of polysaccharides in lignocellulosic materials, comprising contacting the lignocellulosic materials with ammonia at a temperature from about 100° C. to about 200° C., at a pressure from about 6.9 MPa to about 35 MPa, and at an ammonia density from about 0.10 g per mL to about 0.45 g per mL. The present invention also provides products of the foregoing process.

DETAILED DESCRIPTION OF THE INVENTION

As used throughout the specification, "bioavailability" refers to the relative ability of a particular material to be hydrolyzed by cellulase and related enzymes, or, in the alternative, to the relative utility of a particular material as a carbohydrate source in microbial fermentation. Thus, materials with increased bioavailability, as that term is employed herein, are more readily hydrolyzed by cellulases, or more readily degraded and metabolized by microbial activity. "Polysaccharide," as employed throughout the specification, refers to polymeric constituents of lignocellulosic materials which comprise repeating monosaccharide units. Exemplary polysaccharides include cellulose in the various forms found in lignocellulosic materials, and hemicelluloses such as xylans, mannans, and galactans. As used herein, "lignocellulosic materials" refers generally to plant tissue, particularly structural plant tissue comprising complex associations of polysaccharides and lignin. Exemplary materials within this definition include agricultural waste materials and by-products, hardwoods and softwoods.

Suitable agricultural waste materials and by-products to be treated by the process of the present invention can be derived from any source. Examples of such materials include cornstalks, corn cobs, wheat, oat, and barley straw, and bagasse. These materials are generally considered poor fodder for animals or poor substrates for rapid microbial fermentation, due the relative indigestibility of cellulose and related polysaccharides, which are the principal components of these materials. However, following treatment by the process of the present invention, more than 90 percent of the available polysaccharides in the form of cellulose and hemicelluloses can be converted to monosaccharides by cellulases.

Suitable woody materials can likewise be derived from any source. However, hardwoods or deciduous woods are generally more effectively treated by the process of the present invention than softwoods, or coniferous woods. For this reason, hardwoods are preferred lignocellulosic materials for treatment and subsequent bioconversion. Representative hardwoods include wood derived from trees of the genera Acer, Quercus, Populus, Betula, Alnus, Fagus, and Liquidambar.

Materials to be treated in accordance with the process of the present invention should generally be coarsely chipped or shredded to facilitate handling in bulk. However, fine milling, or other mechanical reduction to a small particle size, is not required to obtain successful results. This aspect of the present invention tends to distinguish it from other processes involving milling and extensive mechanical processing steps.

Generally, the process of the present invention is conducted within a sealed reactor or retort arranged to enable recovery of gaseous ammonia upon pressure reduction at the conclusion of treatment.

The critical variables to be monitored in treating lignocellulosic materials include temperature, pressure, and ammonia density. Each of these parameters must be maintained within prescribed limits to attain supercritical or near-supercritical states for fluid ammonia, with the attendant advantages in treatment efficacy. Thus, process temperatures should be maintained between about 100° C. and about 200° C., preferably from about 135° C. to about 165° C. For best results, this temperature should be maintained from about 30 seconds to about 60 minutes.

Process pressures are maintained from about 6.9 MPa (1000 psi) to about 35 Mpa (5000 psi); preferably from about 8.3 MPa (1200 psi) to about 17.2 MPa (2500 psi). Ammonia densities are maintained from about 0.10 g per mL to about 0.45 g per mL, and preferably from about 0.20 g per mL to about 0.40 g per mL.

Following treatment in accordance with the process of the present invention, the resulting products can be further processed by enzymatic hydrolysis to provide mixtures of monosaccharides suitable for fermentation to ethanol by yeast, or used directly as carbohydrate sources in a variety of fermentation or bioconversion processes involving other organisms. Alternatively, the products of the process of the present invention can be used directly as substrates in fermentation processes.

Additional washing or treatment steps are typically not required following treatment with supercritical ammonia. Modest residues of ammonia are not harmful in subsequent fermentation steps, and can provide a beneficial nitrogen source.

Preferred enzymes for hydrolysis are cellulases and hemicellulases, of which the most preferred are associated with the cellulase complex of the fungus *Trichoderma reesei*. If the products of the present invention are employed directly in fermentation processes, thermophilic bacteria such as *Clostridium thermocellum* are useful. Finally, preliminary experiments have suggested that the products of the process of the present invention can be fed to livestock.

The following examples illustrate various aspects of the present invention. In the examples, all parts are by weight unless otherwise indicated, and all degrees are Celsius (°C.)

EXAMPLE 1

White birch chips (*Betula papyrifera*) were cryogenically ground in a micropulverizer to provide particles of 10 to 12 mesh. One gram of the resulting particles was placed in a 10 mL stainless steel high pressure tube, which was placed in a cold bath and evacuated to an internal pressure of about 3.3 kPa (2.5 mm Hg). 3.11 g of liquid ammonia were then added. The tube was then placed in a rocking electric furnace and gradually heated to 150° over a 40 minute period. This temperature was maintained for 20 minutes. The tube was then removed from the furnace and permitted to cool. At 150°, the internal pressure in the tueb was estimated to be about 13.8 MPa (2000 psi). At this temperature and pressure, the ammonia contained within the tube existed as a supercritical fluid, since the temperature exceeded 132.4°, the pressure exceeded 11.2 MPa (1636 psi), and the density of the ammonia exceeded 0.235 g/mL.

As a result of this treatment, the birch wood turned dark in color. To determine the sensitivity of this material to enzymatic degradation, 100 mg of the ammoniated birch wood particles were neutralized by dropwise addition of 0.1 N HCl, and then incubated in a mixture containing 1.3 mL 0.05 M sodium acetate buffer, pH 4.8, 0.2 mL of a cellulase solution containing a total of 0.334 IU (International Units), and 8.5 mL water, for 24 hours at 50°, with constant stirring. As a result of the incubation with enzyme, 91 percent of the available cellulose in the sample was hydrolyzed to glucose, and 78 percent of the available xylan was hydrolyzed to xylobiose and xylose.

To determine the sensitivity of the lignocellulosics in the treated wood sample to degradation by microbial fermentation, a sample was employed as a substrate for growth of *Clostridium thermocellum* as described below.

A sample of the treated birch particles was added to GS2 medium (see below) to provide a concentration between 0.61 and 0.73 percent (w/v).

| GS2 Medium | |
| --- | --- |
| $KH_2PO_4$ | 0.25 g |
| $K_2HPO_4$ (anhydrous) | 0.38 g |
| Urea | 2.0 g |
| $MgCl_2 6H_2O$ | 0.20 g |
| $CaCl_2 2H_2O$ | 0.10 g |
| $FeSO_4 6H_2O$ | 1.25 mg |
| MOPS buffer (free acid) (morpholinopropanesulfonic acid) | 10.0 g |
| yeast extract | 5.0 g |
| $H_2O$ to | 1.0 L |

0.02 mg dry bacterial cells were added per mL culture medium, and the resulting culture was incubated at 60° for 9 days. As a result of this fermentation, dry weight of substrate was reduced 59.9 percent. A control fermentation, using particles of white birch which had not been treated by supercritical ammonia, sustained a loss in dry weight of only 3.8 percent.

EXAMPLE 2

Micropulverized particles of white birch were treated with ammonia substantially as described in Example 1, above, except that the amount of ammonia added to the high pressure tube was 1.31 g.

To determine the susceptibility of the carbohydrates in the resulting sample to enzymatic hydrolysis, a digestion with cellulase was carried out substantially as described in Example 1. The resulting yield of glucose from cellulose was 76.2 percent, and the yields of xylobiose and xylose from xylan were 36.5 and 30.0 percent, respectively.

EXAMPLE 3

This example demonstrates that supercritical ammonia pretreatment of white birch particles is not significantly affected by their moisture content. Twelve samples of white birch, having moisture contents varying between 8 and 50 percent, were treated with supercritical ammonia substantially as described in Example 1, except that 3.0 g ammonia were added to the pressure tube for each treatment, and the tubes were incubated for 20 minutes at 175°. The resulting samples of treated white birch were then incubated with cellulase substantially as described in Example 1. The amount of cellulose converted to monosaccharides by cellulase varied between about 50 and about 95 percent; however, no significant correlation between extent of conversion and moisture content of starting materials was observed.

EXAMPLE 4

This example indicates that the process of the present invention is capable of rendering a variety of lignocellulosic materials susceptible to direct hydrolysis by cellulases.

Samples of aspen (*Populus tremuloides*), southern red oak (*Quercus falcata*), and sweet gum (*Liquidambar styraciflua*) were selected as representative hardwoods, while samples of corn stalks, corn cobs, and bagasse were obtained as representative agricultural by-products. Each sample was ground to provide particles capable of passing a 10 mesh sieve. 1.0 g samples of each material were subjected to supercritical ammonia treatment, substantially as described in Example 3. The resulting treated materials were then incubated with cellulase substantially as described in Example 1. The results obtained are set forth in Table I, below. Values greater than 100 percent are attributable to use of literature values for cellulose content of starting materials (sweet gum, corn cobs) or to use of averages of several determinations.

TABLE I

Effect of Supercritical Ammonia Treatment upon Susceptibility of Various Lignocellulosics to Cellulase and Xylanase Hydrolysis

| Sample | Cellulose Hydrolyzed to Glucose (%) | Xylan Hydrolyzed to Xylose and Xylobiose (%) |
| --- | --- | --- |
| Aspen | 105.2 | 75.8 |
| Red Oak | 101.7 | 84.4 |
| Sweet Gum | 106.4 | 64.7 |
| Corn Stalks | 98.5 | 89.1 |
| Corn Cobs | 112.0 | 104.2 |
| Bagasse | 84.1 | 72.5 |

EXAMPLE 5

This example illustrates the process of the present invention in operation on a larger experimental scale. 50 g of southern red oak particles (20–40 mesh) and 5 g of oak chips were placed into a 500 mL autoclave, which was then sealed and evacuated to about 2.7–4.0 kPa (2–3 mm Hg). 175 g ammonia were added, and the autoclave was immersed in hot water to rapidly raise the internal temperature to about 50° The autoclave was then placed in a rocking electric furnace which had been preheated to provide a temperature of 160°. The internal temperature of the autoclave was then raised to 150° over a period of 11 minutes by injecting live steam into its internal heating coils. The internal temperature of the autoclave was maintained at 150° for 20 minutes, generating an internal pressure of 14.13 MPa (2050 psi).

The reactor was then cooled rapidly by circulating cooling water through the internal coils.

The resulting treated oak particles were then incubated with cellulase substantially as described in Example 1. Following 24 hours incubation, 87.6 percent of available cellulose was converted to glucose, and 74.2% of available xylan was converted to xylose and xylobiose. A substantially similar control incubation using untreated southern red oak particles resulted in a 6.9 percent conversion of cellulose to glucose, and an 8.0 percent conversion of xylan to xylose and xylobiose.

EXAMPLE 6

This example indicates that lignocellulosic materials need not be finely pulverized to be effectively treated by the process of the present invention. Chips of southern red oak having dimensions of about 2.5 cm by 2.5 cm by 1 cm were subjected to supercritical ammonia treatment substantially according to the method of Example 5. The treated chips were ground to particles capable of passing a 10 mesh sieve and then incubated with cellulase substantially as described in Example 1. 92.2 percent of the available cellulose was converted to glucose, and 78.3 percent of the available xylan was hydrolyzed to xylose and xylobiose.

EXAMPLE 7

This example illustrates effects of variations in ammonia concentration and temperature. Specifically, optimal treatment effectiveness is attained at high ammonia densities and at temperatures between about 125° and 175°.

A series of treatments were conducted as follows. One gram of white birch particles capable of passing a 10 mesh screen was placed in a stainless steel high pressure tube. Ammonia was added to provide a preselected density, and then the tube was sealed and placed in a rocking furnace. The tube was heated to a preselected temperature over a period of about 30 minutes, and held at that temperature for an additional 20 minutes. The reactor tube was then removed from the furnace and permitted to cool to about 23°. One hundred milligrams of the resulting treated material were then isolated and neutralized by addition of dilute HCl. The neutralized sample was then digested with cellulase, substantially as described in Example 1, above. The results of this series of experiments are set forth in Table II, below.

TABLE II

Effects of Varying Ammonia Density and Temperature Upon Digestibility of White Birch by Cellulose

| Ammonia Density (g/mL) | Percent of Cellulose in Sample Converted to Glucose Temperature (°C.) | | | | |
| --- | --- | --- | --- | --- | --- |
| | 100 | 125 | 150 | 175 | 200 |
| 0.01 | 26.8 | 17.4 | 21.8 | 23.8 | 13.8 |
| 0.05 | 52.5 | 57.3 | 44.5 | 40.6 | 40.3 |
| 0.10 | 57.7 | 64.6 | 72.3 | 50.5 | 22.9 |
| 0.20 | 54.2 | 58.2 | 76.0 | 49.4 | 36.5 |
| 0.30 | 44.7 | 73.2 | 90.8 | 62.8 | 47.3 |

EXAMPLE 8

This example indicates that lignocellulosic materials pretreated by supercritical ammonia are capable of being digested by bovine rumen fluid. This observation suggests that lignocelluosic materials treated by supercritical ammonia can be employed as fodder for ruminant animals.

Several lignocellulosic materials were selected for evaluation in the following experiments. A sample of each material was subjected to supercritical ammonia treatment substantially as described in Example 1, above, except that the ammonia density employed was 0.3 g per mL, and each sample was heated at 150° for approximately 20 minutes, except for a white birch sample, which was heated at 175° for 20 minutes.

Bovine rumen fluid was obtained from a fistulated cow approximately 4 to 5 hours following a morning feeding of hay. The sample of rumen fluid was maintained at 39° in a Dewar flask containing a $CO_2$ gas phase. Prior to use, the fluid was filtered through three layers of cheesecloth; however, care was taken to maintain the fluid sample under an atmosphere of $CO_2$ to the extent possible.

In the experiments reported in Table III, below, 250 mg samples of wood particles treated by supercritical ammonia were added to individual 50 mL (150 mm × 25 mm) screw cap tubes containing 3 mL water. Each tube was then placed under vacuum for 15 minutes, and then 17.5 mL McDougall buffer (McDougall, *Biochem. J.* 43:99 (1948)) were added. Any air in the tubes was displaced by $CO_2$, and 17.5 mL rumen fluid were added to each tube. The tubes were then sealed and incubated at 39° for 94 hours. The tubes were incubated in a horizontal position, and were gently agitated 4 times each day; however, the tubes were allowed to remain undisturbed during the remainder of the incubation period. To release accumulated gases, the cap of each tube was briefly loosened once each day.

At the conclusion of the incubation period, the contents of each tube were transferred to preweighed 50 mL polypropylene centrifuge tubes and centrifuged at 1800×g for 15 minutes. The supernatant fluids were then decanted and discarded. Each tube was then weighed. The difference between sample starting weight and the weight of the residue following digestion was assumed to correspond to the amount of material digested. Control experiments were run using untreated wood samples, and samples were also digested by *C. thermocellum* for comparison, substantially as described in Example 1. The results are set forth in Table III, below.

TABLE III

Effects of Supercritical Ammonia Treatment Upon Digestibility of Lignocellulosic materials by Bovine Rumen Fluid and *C. thermocellum* Fermentation

| Sample | | Dry Weight Loss in Percent | |
|---|---|---|---|
| | | Rumen Fluid | *C. thermocellum* Fermentation |
| White birch | untreated | 3.6 | 3.8 |
| | treated | 39.1 | 59.9 |
| Soft Maple | untreated | 6.7 | 3.0 |
| | treated | 42.2 | 49.7 |
| Red Oak | untreated | 7.5 | 0.0 |
| | treated | 46.3 | 21.7 |
| Aspen | untreated | — | 10.2 |
| | treated | — | 43.3 |

What is claimed is:

1. A process for improving the bioavailability of polysaccharides in lignocellulosic materials, comprising contacting the lignocellulosic materials with ammonia at a temperature from about 100° C. to about 200° C., at a pressure from about 6.9 MPa to about 35 MPa, and at an ammonia density from about 0.10 g per mL to about 0.45 g per mL.

2. A process according to claim 1, conducted for period from about 30 seconds to about 60 minutes.

3. A process according to claim 2, wherein the temperature is from about 135° C. to about 165° C.

4. A process according to claim 3, wherein the pressure is greater than about 8.3 MPa.

5. A process according to claim 4, wherein the pressure is maintained from about 8.3 MPa to about 17.2 MPa.

6. A process according to claim 5, wherein the ammonia density is maintained from about 0.20 g per mL to about 0.40 g per mL.

7. A process according to claim 6, conducted for a period from about 2 to about 30 minutes.

8. A process according to claim 7, wherein the lignocellulosic materials are agricultural byproducts.

9. A process according to claim 8, wherein the lignocellulosic materials are cornstalks or corncobs.

10. A process according to claim 8, wherein the lignocellulosic materials are bagasse.

11. A process according to claim 7, wherein the lignocellulosic materials are wood fragments.

12. A process according to claim 11, wherein the lignocellulosic materials are hardwood fragments.

13. A product of the process of claim 1.
14. A product of the process of claim 6.
15. A product of the process of claim 7.
16. A product of the process of claim 8.
17. A product of the process of claim 9.
18. A product of the process of claim 10.
19. A product of the process of claim 11.
20. A product of the process of claim 12.

* * * * *